(12) United States Patent
Kim et al.

(10) Patent No.: US 12,005,152 B2
(45) Date of Patent: Jun. 11, 2024

(54) MICROGEL COMPOSITION COMPRISING COLLAGEN AND METHOD OF PREPARING THE SAME

(71) Applicant: KOREA INSTITUTE OF SCIENCE AND TECHNOLOGY, Seoul (KR)

(72) Inventors: Sang-Heon Kim, Seoul (KR); Seung Ja Oh, Seoul (KR); Ha Eun Chung, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 166 days.

(21) Appl. No.: 17/168,780

(22) Filed: Feb. 5, 2021

(65) Prior Publication Data

US 2021/0244847 A1    Aug. 12, 2021

(30) Foreign Application Priority Data

Feb. 7, 2020    (KR) .......................... 10-2020-0015206

(51) Int. Cl.
*A61L 26/00*    (2006.01)
(52) U.S. Cl.
CPC ....... *A61L 26/0033* (2013.01); *A61L 26/0023* (2013.01); *A61L 26/008* (2013.01); *A61L 2300/236* (2013.01); *A61L 2300/252* (2013.01); *A61L 2300/412* (2013.01); *A61L 2300/60* (2013.01)
(58) Field of Classification Search
CPC ............. A61L 26/0033; A61L 26/0023; A61L 26/008; A61L 27/26
See application file for complete search history.

(56) References Cited

U.S. PATENT DOCUMENTS

| 2004/0044416 A1* | 3/2004 | Callegaro ........... A61L 27/3852 |
| | | 623/23.76 |
| 2008/0102114 A1* | 5/2008 | Koritala ............... A61K 9/5031 |
| | | 424/490 |
| 2015/0064147 A1* | 3/2015 | Pollock ................. A61Q 19/08 |
| | | 424/574 |
| 2016/0114003 A1* | 4/2016 | Gennari ............... A61K 31/728 |
| | | 424/618 |
| 2020/0101194 A1 | 4/2020 | Kim et al. |
| 2020/0179287 A1* | 6/2020 | Medina .............. A61K 31/4409 |

FOREIGN PATENT DOCUMENTS

| KR | 10-2007-0089490 A | 8/2007 |
| KR | 10-2009-0131432 A | 12/2009 |
| KR | 10-2013-0018518 A | 2/2013 |
| KR | 10-2013-0083596 A | 7/2013 |
| KR | 10-1340458 B1 | 12/2013 |
| KR | 10-2019-0016535 A | 2/2019 |
| KR | 10-2020-0039055 A | 4/2020 |
| WO | WO-2019094526 A1 * | 5/2019 ........... A61L 15/225 |

OTHER PUBLICATIONS

International Search Report dated Jul. 7, 2021, in PCT/KR2021/001569.

* cited by examiner

*Primary Examiner* — Robert A Wax
*Assistant Examiner* — William Craigo
(74) *Attorney, Agent, or Firm* — Birch, Stewart, Kolasch & Birch, LLP (57) ABSTRACT

The present disclosure relates to a microgel composition comprising collagen and hyaluronic acid and a method of preparing the same. The microgel according to an embodiment is composed of natural biocompatible substances and is non-toxic and has high mechanical stability or long persistence, and thus can be effectively used in a microgel composition, a three-dimensional scaffold composition, and a tissue-engineering scaffold.

8 Claims, 12 Drawing Sheets

MICROGEL COMPOSITION COMPRISING COLLAGEN AND METHOD OF PREPARING THE SAME

CROSS-REFERENCE TO RELATED APPLICATION

This application is based on and claims priority under 35 U.S.C. § 119 to Korean Patent Application No. 10-2020-0015206, filed on Feb. 7, 2020, in the Korean Intellectual Property Office, the disclosure of which is incorporated by reference herein in its entirety.

BACKGROUND

1. Field

The present disclosure relates to a microgel composition comprising collagen and hyaluronic acid and a method of preparing the same.

2. Description of Related Art

A microgel is a micro-sized hydrogel and is produced by constructing a network structure by chemically or physically crosslinking a hydrophilic polymer. In general, a microgel is prepared by dispersing an inner phase containing a hydrophilic polymer in an outer phase containing a surfactant and crosslinking the inner phase. Meanwhile, since a microgel is made in a variety of sizes and shapes and physical properties thereof, such as crosslinking density, are controllable, the microgel may be a good candidate for a cell support. Therefore, thus far, research into beta-glucan-based hydrogels is still at an early stage.

The hydrogels have high hydrophilicity and thus absorb water, and the strength or shape thereof can be changed easily, thus allowing their use as a scaffold for tissue engineering or drug delivery. Due to the hydrophilicity of its constituents, a hydrogel absorbs a great deal of water in an aqueous solution or in an aqueous environment and swells, but does not dissolve due to its crosslinked structure. Therefore, hydrogels having a variety of shapes and properties may be produced according to constituents and preparation methods. In addition, hydrogels generally contain a large amount of water, and thus may have intermediate properties between a liquid and a solid.

Meanwhile, collagen widely used as a biocompatible polymer of a hydrogel is the most common protein found in humans and is abundantly present in mammals, and makes up about 25-35% of all the proteins of the body. Particularly, collagen is an important component of bones, tendons, and ligaments and primarily functions to maintain the structure of organs. Collagen may be easily extracted from the skin of cows or pigs. In addition, hyaluronic acid is the most widely used natural polymer and exists in connective tissues of skin, cartilages, bones, synovial fluids, etc. Hyaluronic acid has viscoelasticity, non-immunogenic response, biocompatibility, and swelling characteristics, and thus has excellent features for use as a biomaterial. Therefore, hyaluronic acid may be useful in various applications, such as viscosupplementation, drug delivery, and scaffolds for wound healing.

Accordingly, the present inventors completed the present disclosure by confirming the optimal proportion of collagen and hyaluronic acid for a microgel to be effectively prepared without a chemical crosslinking agent.

SUMMARY

An aspect provides a microgel composition comprising 7.5% (w/v) to 20% (w/v) of collagen and 1% (w/v) to 5% (w/v) of hyaluronic acid.

One aspect is to provide a three-dimensional scaffold comprising 7.5% (w/v) to 20% (w/v) of collagen and 1% (w/v) to 5% (w/v) of hyaluronic acid.

Another aspect is to provide a support for tissue engineering, comprising 7.5% (w/v) to 20% (w/v) of collagen and 1% (w/v) to 5% (w/v) of hyaluronic acid.

Still another aspect is to provide a method of preparing a microgel composition comprising: forming electrostatic collagen-hyaluronic acid complex by mixing 7.5% (w/v) to 20% (w/v) of collagen with 1% (w/v) to 5% (w/v) of hyaluronic acid; preparing a dispersion of a microgel by breaking the collagen-hyaluronic acid complex; and subjecting the dispersion of the microgel to natural sedimentation.

Additional aspects will be set forth in part in the description which follows and, in part, will be apparent from the description, or may be learned by practice of the presented embodiments of the disclosure.

In an aspect, provided is a microgel composition comprising 7.5% (w/v) to 20% (w/v) of collagen and 1% (w/v) to 5% (w/v) of hyaluronic acid.

In one aspect, provided is a three-dimensional scaffold comprising 7.5% (w/v) to 20% (w/v) of collagen and 1% (w/v) to 5% (w/v) of hyaluronic acid.

In another aspect, provided is a support for tissue engineering, comprising 7.5% (w/v) to 20% (w/v) of collagen and 1% (w/v) to 5% (w/v) of hyaluronic acid.

As used herein, the term "hydrogel" may mean a three-dimensional network structure formed by crosslinking hydrophilic polymers via covalent or non-covalent bonds. Due to hydrophilicity of constituents, hydrogels swell by absorbing a large amount of water in an aqueous solution or under an aqueous environment, but are not readily dissolved because of a crosslinking structure thereof. Therefore, depending on constituents and preparation methods, hydrogels having various types and properties may be prepared. In addition, hydrogels, containing a large amount of water, are generally characterized by having an intermediate nature of a liquid and a solid. Specifically, a microgel is a micro-sized hydrogel and is produced by constructing a network structure by chemically or physically crosslinking a hydrophilic polymer.

The collagen is the most common protein found in humans and is most abundantly present in mammals, which comprises about 25-35% of all the proteins of the body. Particularly, collagen is an important component of bones, tendons, and ligaments and primarily maintains the structure of organs, and may be easily extracted from the skin of cows or pigs. The collagen may comprise, in addition to pure collagen, collagen derivatives. With regard to the collagen, types (origins) thereof are not particularly limited, and a variety of collagens derived from, for example, mammals or fish, such as cow bone, cow skin, pig bone, pig skin, etc. In addition, the collagen may have a molecular weight of 100,000 to 250,000, 120,000 to 240,000, or 150,000 to 200,000.

As used herein, the term "hyaluronic acid (HA)" is interchangeably used with "hyaluronan", "hyaluronate" or "HA", and the hyaluronic acid may be represented by Formula 1 and may include a pharmaceutically acceptable salt thereof, such as sodium hyaluronate (NaHA), potassium hyaluronate, magnesium hyaluronate, and a combination thereof.

(1)

wherein, in Formula 1, n is the number of repeating units. Hyaluronic acids of all origins, including bacteria and avian origins, are useful. Such useful hyaluronic acids may have a range of molecular weight of from about 0.3 million Daltons (MDa) to about 6.0 MDa, for example, about 1.5 MDa to about 6.0 MDa, about 2.5 MDa to about 6.0 MDa, about 3.5 MDa to about 6.0 MDa, about 0.3 MDa to about 5.0 MDa, about 0.3 MDa to about 4.0 MDa, or about 0.3 MDa to about 3.0 MDa.

Therefore, in the microgel composition, the three-dimensional scaffold and tissue engineering support compositions, or the bio-ink composition, according to one or more specific embodiments, the composition may not substantially contain an additional crosslinking agent.

As used herein, the expression "does not contain", "is free of", or "substantially free of" indicates that a crosslinking agent, e.g., a chemical crosslinking agent, is not included in an effective amount, i.e., it is present in an amount insufficient to perform its complete role. Specifically, the crosslinking agent is present in an amount of less than about 1% by weight, less than about 0.5% by weight, less than about 0.1% by weight, and, in some cases, less than about 0.05% by weight, and in other cases, none, with respect to the total amount of the composition.

In an aspect, the collagen may be contained in an amount of about 7.5-12.5% (w/v) with respect to the total amount of the composition. Specifically, the collagen may be contained in an amount of about 8-12% (w/v), about 8.5-11.5% (w/v), about 9-11% (w/v), or about 9.5-10.5% (w/v), or, for example, about 10% (w/v).

In an aspect, the hyaluronic acid may be contained in an amount of about 1-5% (w/v) with respect to the total amount of the composition. Specifically, the hyaluronic acid may be contained in an amount of about 2-4.5% (w/v), about 2-4% (w/v), about 2.5-3% (w/v), about 3.5-4% (w/v), or about 2.5% (w/v).

The microgel contained in the composition may have a size of, for example, 10 μm to 250 μm, 20 μm to 200 μm, 10 μm to 50 μm, 20 μm to 40 μm, 80 μm to 220 μm, or 100 μm to 200 μm.

In addition, the composition may have a pH range of 4 to 11, and when the composition is in the above pH range, the microgel composition may have a zeta potential of −50 mV to −30 mV.

In another specific embodiment, the composition may be a cell-laden microgel. In addition, the composition may further include growth factors or differentiation factors. The cells to be cultured with microgel may include cells, tissues, cells to be differentiated into other cell types, or other cells to be used for tissue regeneration. Examples of the cells may be stem cells, sensory cells, brain cells, germ cells, epithelial cells, immune cells, cancer cells or combinations thereof. The stem cell may mean a cell having differentiation potency, and the cell having differentiation potency may be, for example, a blast cell, a hepatocyte, a fibroblast, a muscular cell, an adult stem cell, a mesenchymal stem cell, a lipid derived mesenchymal stem cell, a bone marrow-derived mesenchymal stem cell, a nerve-derived mesenchymal stem cell, a placenta-derived mesenchymal stem cell, an umbilical cord blood stem cell, or a combination thereof. The growth factor may mean a substance capable of regulating the growth and function of a cell. The differentiation factor may mean a substance that induces differentiation of a cell into another cell type. Examples of the growth factor or the differentiation factor may include a transforming growth factor (TGF), a vascular endothelial growth factor (VEGF), a fibroblast growth factor (FGF), an epidermal growth factor (EGF), a platelet-derived growth factor (PDGF), a hepatocyte growth factor (HGF), an insulin-like growth factor (IGF), cytokine, chemokine, or combinations thereof.

The three-dimensional scaffold may be is in the form of: a nonwoven fabric; a woven fabric; a knitted fabric; a fiber bundle; a cylinder including a fiber bundle and a tube into which the fiber bundle is inserted; or a combination of two or more thereof. The scaffold may perform a function, such as cell cultivation, cell delivery or drug delivery, using spaces formed by fibers included in such a fiber structure.

As used herein, the term "tissue-engineering scaffold" means a substance capable of substituting some of damaged internal organs or tissues of the body and compensating or replacing functions thereof. Specifically, the scaffold may include a biocompatible polymer. Accordingly, the polymer scaffold may be retained until the scaffold sufficiently performs the function and role thereof, and may then be completely biodegraded and removed from body.

In order for the tissue-engineering scaffold of the present disclosure to perform the function of substituting a living body for a given period of time, the tissue-engineering scaffold is preferred to be physically stable. For instance, conjugating polyphenols to polymers hyaluronic acid was reported to improve resistance to hyaluronidase, antimicrobial activity and oxidation and thus can be used as a highly stable tissue-engineering scaffold.

The composition may comprise a therapeutically effective amount of at least one anesthetic, for example, lidocaine.

The composition according to a specific embodiment is biocompatible, and thus may induce semi-permanent tissue regeneration to a cell so as to be effectively used for a three-dimensional scaffold or a tissue-engineering scaffold. In addition, once introduced into a skin, the composition may be sustained in the skin, for example, for three months or more, six months or more, or for a maximum of up to a year.

In another aspect, provided is a method of preparing a microgel composition comprising the steps of: forming an electrostatic collagen-hyaluronic acid complex by mixing 7.5% (w/v) to 20% (w/v) of collagen with 1% (w/v) to 5% (w/v) of hyaluronic acid; preparing a dispersion of a microgel by breaking the collagen-hyaluronic acid complex; and subjecting the dispersion of the microgel to natural sedimentation.

In the method, the subjecting of the dispersion of microgel to natural sedimentation may be performed in a temperature range of 20-30° C., for example, for 12-36 hours, 18-28 hours, 20-26 hours, 22-25 hours, or 24 hours.

The reaction of the obtained non-antigenic collagen or collagen derivative with the hyaluronic acid may be performed by preparing solutions from the non-antigenic collagen or collagen derivative and the hyaluronic acid. The solution may contain the collagen and the hyaluronic acid at concentrations of 7.5% (w/v) to 20% (w/v) and 1% (w/v) to 3% (w/v), respectively, but the concentrations are not limited to those listed herein.

Agitation is an operation for producing a dispersion of microgel comprising collagen and hyaluronic acid, and may be conducted using a common method known in the art, for example, using a homogenizer or a bead beater.

BRIEF DESCRIPTION OF THE DRAWINGS

The above and other aspects, features, and advantages of certain embodiments of the disclosure will be more apparent from the following description taken in conjunction with the accompanying drawings, in which.

EXAMPLE 1

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

Hereinafter, the present disclosure will be described in greater detail with reference to examples. However, these examples are for illustrative purposes only, and the scope of the present disclosure is not limited thereto.

Therefore, the features illustrated in the embodiments described in the present specification are presented by way of example only and do not represent all of the technical ideas of the present disclosure, so that it should be understood that that various equivalents and modifications may exist which can replace the embodiments described in the time of the application.

EXAMPLE 1. PREPARATION OF COLLAGEN MICROGEL

To prepare a microgel suspension comprising collagen only, concentrations of collagen added were varied to prepare a microgel. Specifically, 1% (w/v), 5% (w/v), 7.5% (w/v) and 10% (w/v) of collagen gels were first prepared, and, to break collagen gel into microgel, 10 μL of each collagen gels was added to 1 mL of distilled water and given agitation using a bead beater at 2000 oscillations per minute (opm) for 10 seconds. Thereafter, prepared microgel suspension was subjected to sedimentation and then allowed to stand undisturbed at room temperature for 24 hours to prepare a collagen microgel. Images of prepared microgel suspensions with varying concentrations of collagen after sedimentation, are shown in FIG. 1, and observation of the microgel particles under a light microscope are shown in FIG. 2.

Figure 1:
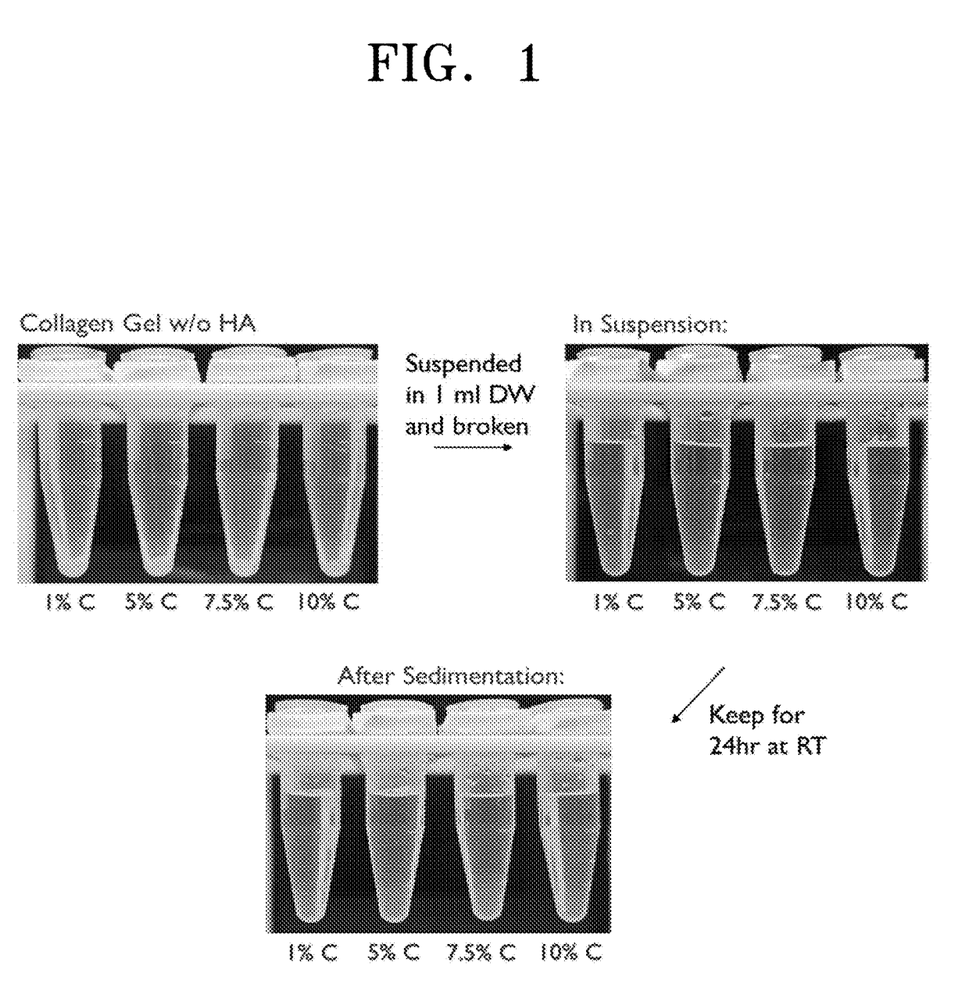
FIG. 1 shows images of microgel suspensions prepared with varying concentrations of collagen and final results of experiments for forming collagen microgels taken after sedimentation.
Figure 2:
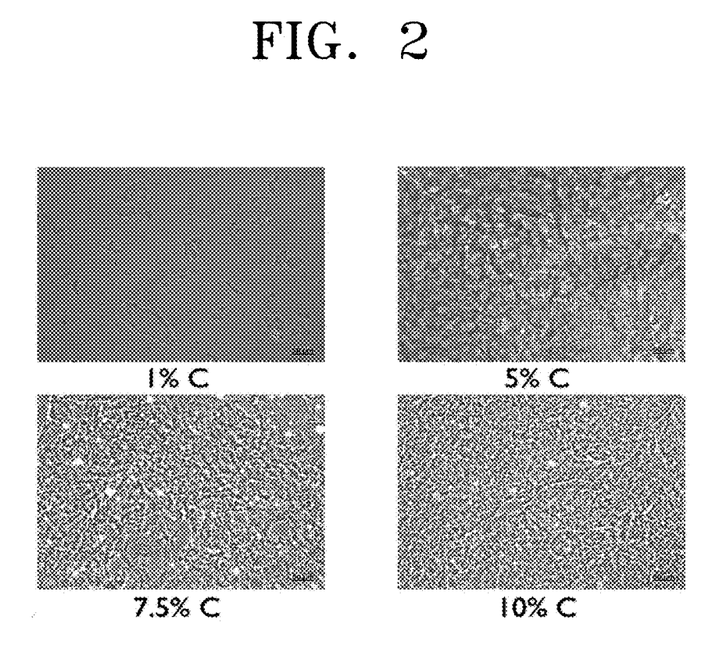
FIG. 2 shows images of microgel suspensions prepared with varying concentrations of collagen and taken under a light microscope.

As confirmed from FIG. 1, prepared collagen hydrogel was broken into microgel by giving agitation using a bead beater, and resulting collagen microgel was translucent and not very apparently visible by naked eye, and the same result was found even after sedimentation. In addition, as confirmed from FIG. 2, it was quite difficult to break collagen hydrogel using a bead beater as the concentrations of collagen in the hydrogels were increased. In particular, it was found that the collagen became more viscoelastic at higher concentrations and thus the crushed collagen had a relatively large particle size, confirming that it gets more difficult to break into microgels as the concentration of collagen was increased. In addition, when the concentration of collagen was low, microgel particles were barely seen in the suspension, which was presumably because collagen fibers had a low density and exhibited little change in fiber thickness.

EXAMPLE 2. PREPARATION OF POLYSACCHARIDE-CONTAINING COLLAGEN MICROGEL

Since it is difficult to prepare a microgel using only collagen, experiments were performed for finding out polysaccharides having negative ions enabling preparation of microgels by forming a complex through electrostatic interaction with collagen while lowering the viscoelasticity of collagen. In this regard, in order to prepare a microgel containing polysaccharides having various charges, chitosan as a positively charged polysaccharide, alginate as a negatively charged polysaccharide or hyaluronic acid were prepared, respectively, and then mixed with collagen gels, thereby finally preparing a collagen hydrogel comprising 10% (w/v) of collagen and 2.5% (w/v) of polysaccharide. 10 µL of the thus prepared collagen-polysaccharide hydrogel was added to 1 mL of distilled water and then broken into microgels through vortexing. The pH levels of resulting microgel suspension were measured, and the microgel suspension was subjected to sedimentation and allowed to stand undisturbed at room temperature for 24 hours to prepare polysaccharide-containing collagen microgels. The polysaccharide-containing collagen microgels and measured values of pH and reported pKa (pI) values of respective microgel suspension are shown in FIG. 3.

Figure 3:
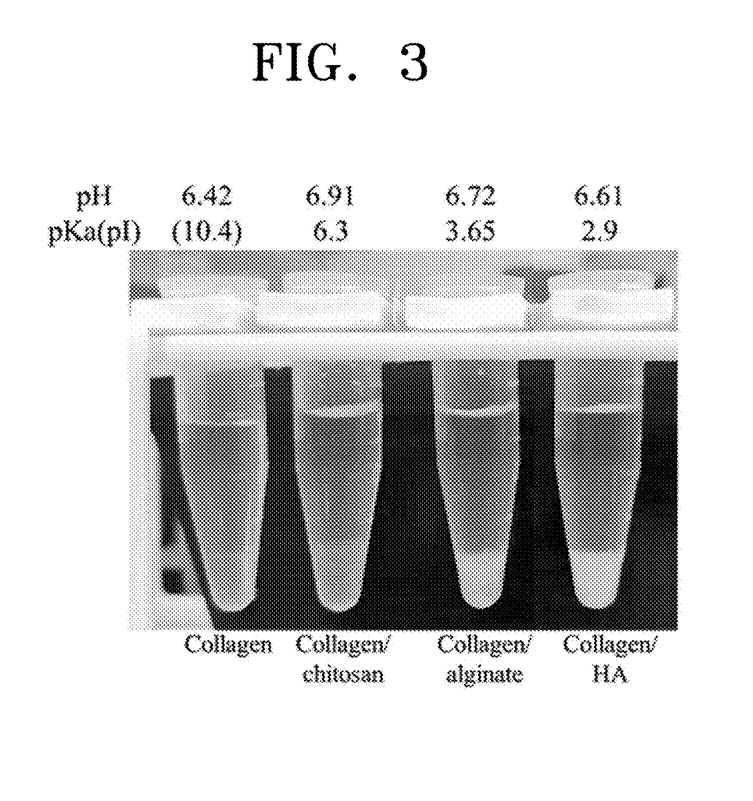
FIG. 3 shows an image of microgel suspensions prepared by adding various polysaccharide, measured pH values and reported pKa (pI) values of each component when the respective microgels are prepared.

As confirmed from FIG. 3, the microgel particles prepared using only collagen hydrogel was not apparently visible by naked eye, and the same result was obtained in the chitosan as a positively charged polysaccharide. However, when a negatively charged polysaccharide is added, it was found that resulting microgel particles appeared as whiter precipitates. Some white precipitates were identified in the negatively charged alginate-containing microgel suspension, and particularly visible when hyaluronic acid was added thereto, as white precipitates, confirming that microgels were effectively prepared when hyaluronic acid, as compared with any other polysaccharide, was added to collagen. To sum up, when collagen is at pH<pI and polysaccharide is at pH>pKa (i.e., when collagen exists as a cation and alginate/HA exist as an anion), the microgel particles are visible as white precipitates.

EXAMPLE 3. IDENTIFICATION OF COLLAGEN CONCENTRATION FOR FORMING OPTIMUM MICROGEL

Figure 4:
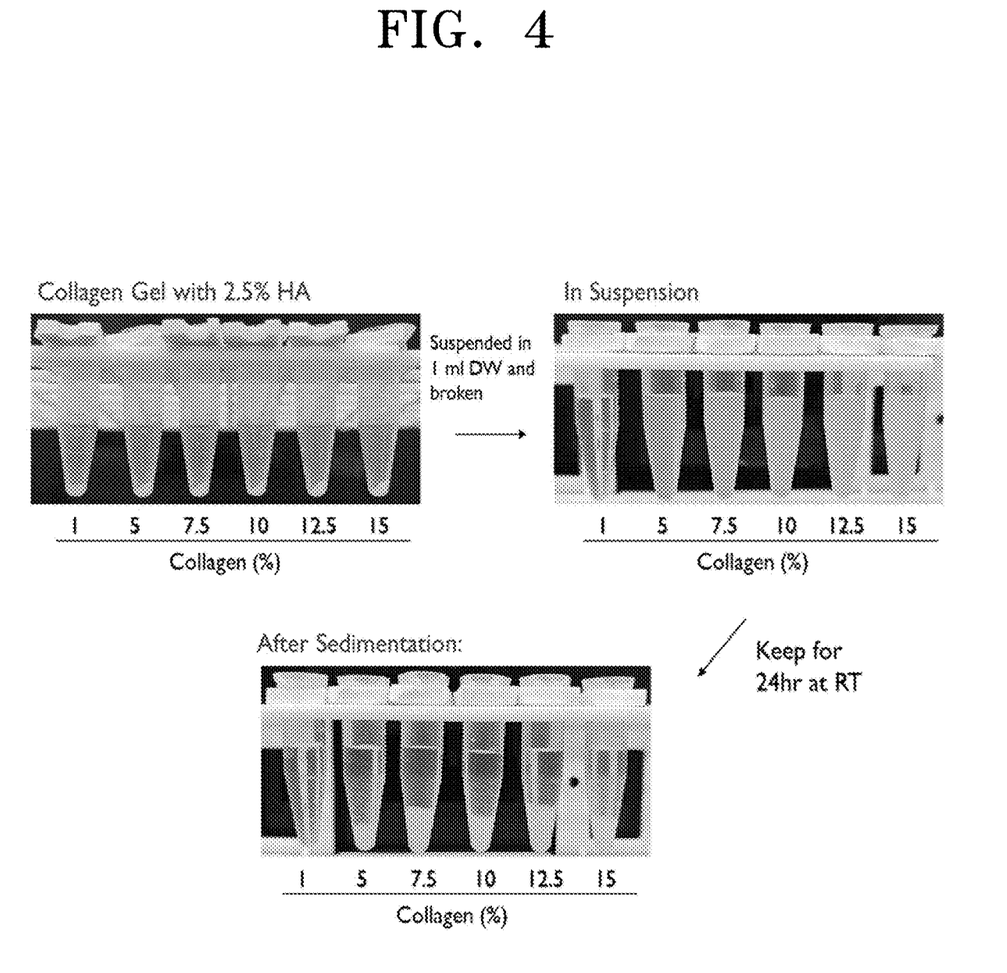
FIG. 4 shows images of collagen-hyaluronic acid microgel suspensions that were prepared by giving agitation to collagen-hyaluronic acid hydrogel with varying concentrations of collagen and concentration of hyaluronic acid, and the resulting collagen microgel suspension after sedimentation.
Figure 5:
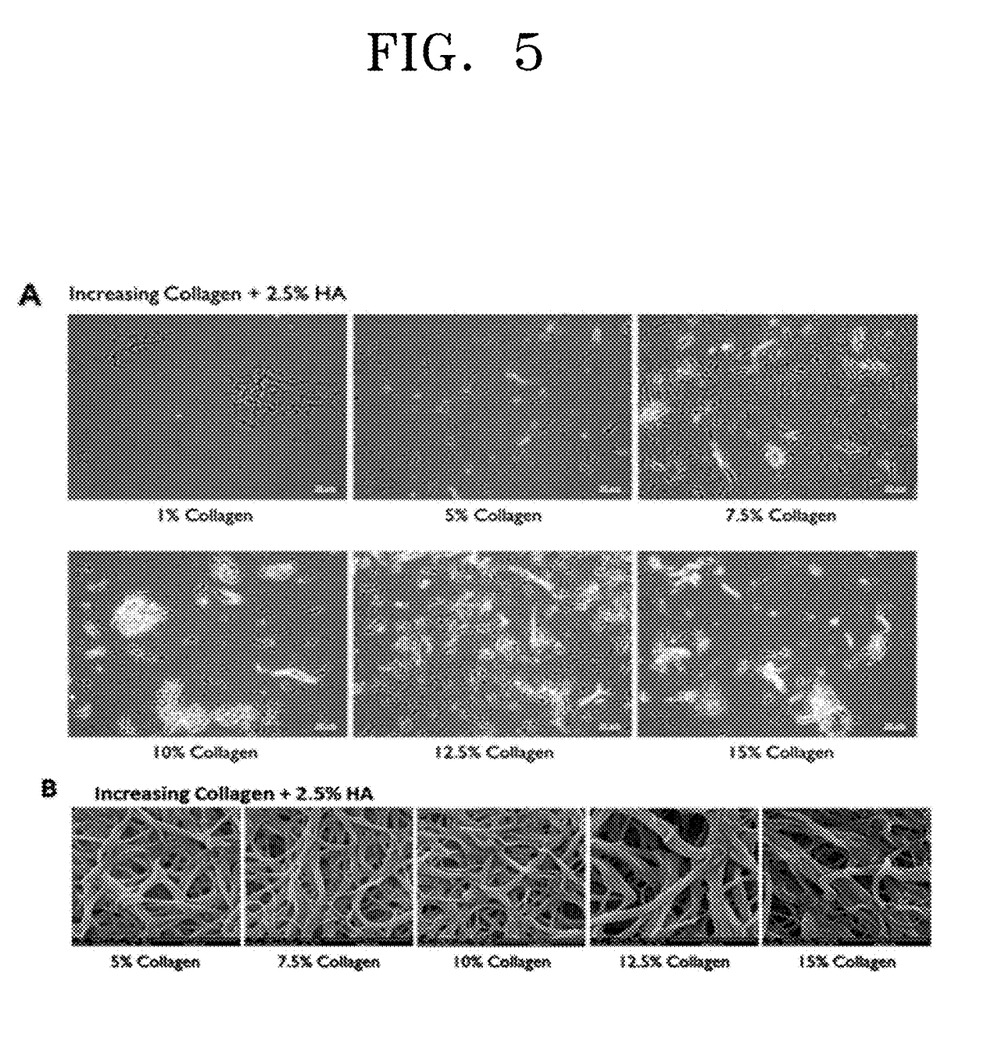
FIG. 5 shows images of collagen-hyaluronic acid microgel suspensions that were prepared by giving agitation to collagen-hyaluronic acid hydrogel with varying concentrations of collagen and concentration of hyaluronic acid. Prepared microgel particles were observed under a light microscope (FIG. 5A), and detailed structures of hydrogels were observed using a scanning electron microscope (SEM) (FIG. 5B)

Experiments were performed to investigate the optimum concentration of collagen to be added to hyaluronic acid through electrostatic interaction with positively charged collagen to produce microgel suspension. Collagens were mixed with hyaluronic acid, thereby finally preparing collagen hydrogel comprising 1% (w/v), 5% (w/v), 7.5% (w/v), 10% (w/v), 12.5% (w/v), and 15% (w/v) of collagen added to 2.5% (w/v) of hyaluronic acid. In order to break prepared hydrogel into microgel suspension, each 10 µL of collagen gel solutions was added to 1 mL of distilled water and broken into a microgel suspension using a bead beater by giving agitation at 2000 opm for 10 seconds. Thereafter, microgel suspension was subjected to sedimentation and then allowed to stand undisturbed at room temperature for 24 hours. Images of collagen-hyaluronic acid microgel suspensions by varying concentrations of collagen before and after sedimentation are shown in FIG. 4. FIG. 5A shows morphology of the collagen-hyaluronic acid microgel as observed under a light microscope while SEM images showing detailed structures of hydrogels are shown in FIG. 5B.

As confirmed from FIG. 4, when 1% (w/v) of collagen was added even with adding 2.5% (w/v) of hyaluronic acid, a white precipitate was not apparently visible, white precipitate was more apparent from 5% (w/v) of collagen added, and a large amount of white precipitate was seen when adding 7.5% (w/v) to 12.5% (w/v) of collagen. As shown in FIGS. 5A and 5B, very little microgel particles were found in microgel suspension made from 1% (w/v) of collagen hydrogel, and it was found that collagen fibers were thicker at higher concentrations of collagen. When 7.5% (w/v) to 12.5% (w/v) of collagen was added, optimal electrostatic interaction between collagen and hyaluronic acid was exhibited, so that more microgel particles were observed. To sum up, it was found that the optimum microgel was prepared when the collagen concentration was 7.5% (w/v) to 12.5% (w/v).

EXAMPLE 4. IDENTIFICATION OF HYALURONIC ACID CONCENTRATION FOR FORMING OPTIMUM MICROGEL

Figure 6A:
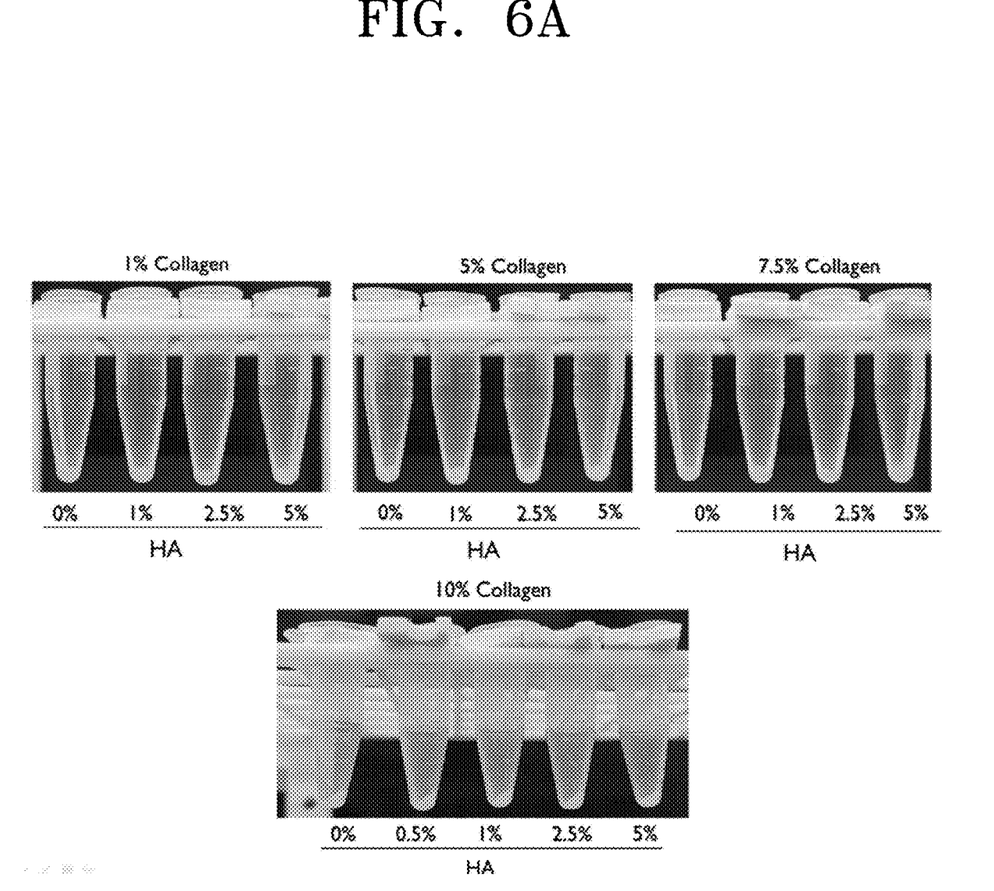
FIG. 6A shows images of microgel prepared with collagen at fixed concentration and hyaluronic acid added at varying concentrations.
Figure 6B:
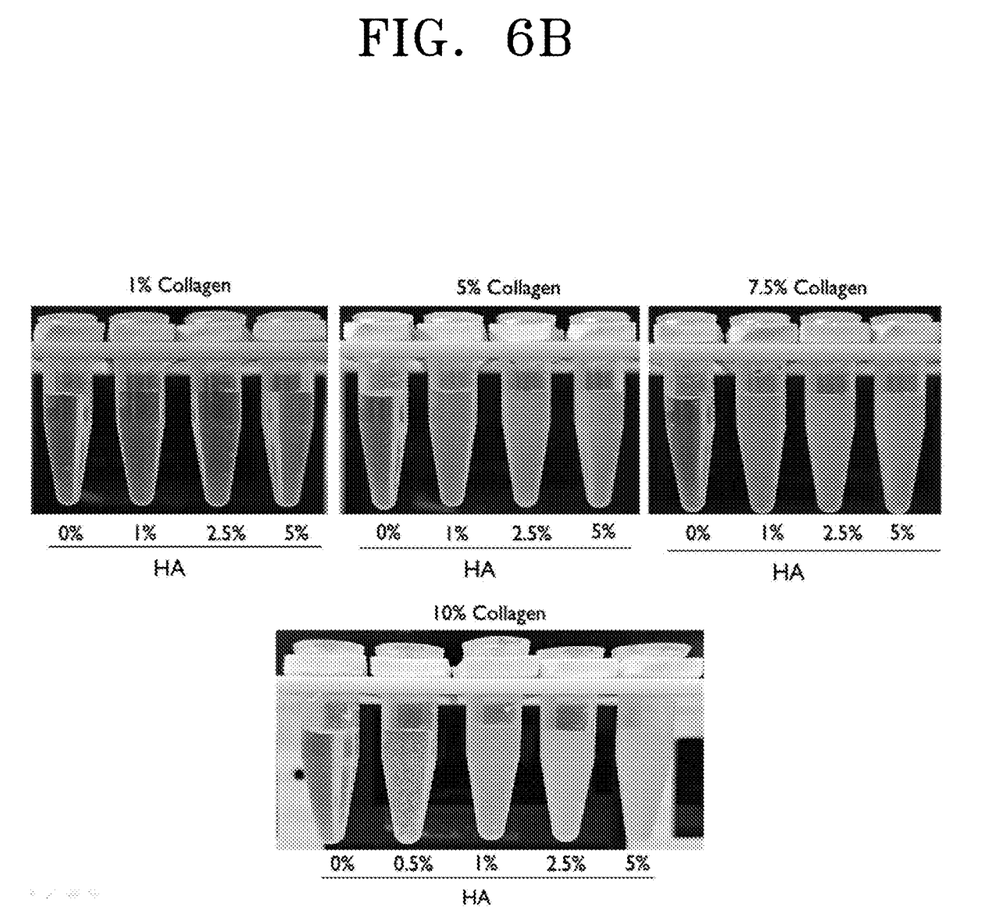
FIG. 6B shows images of microgel suspensions that were prepared with collagen at fixed concentration and hyaluronic acid at varying concentrations and giving agitation to break the resulting hydrogel into microgel.
Figure 6C:
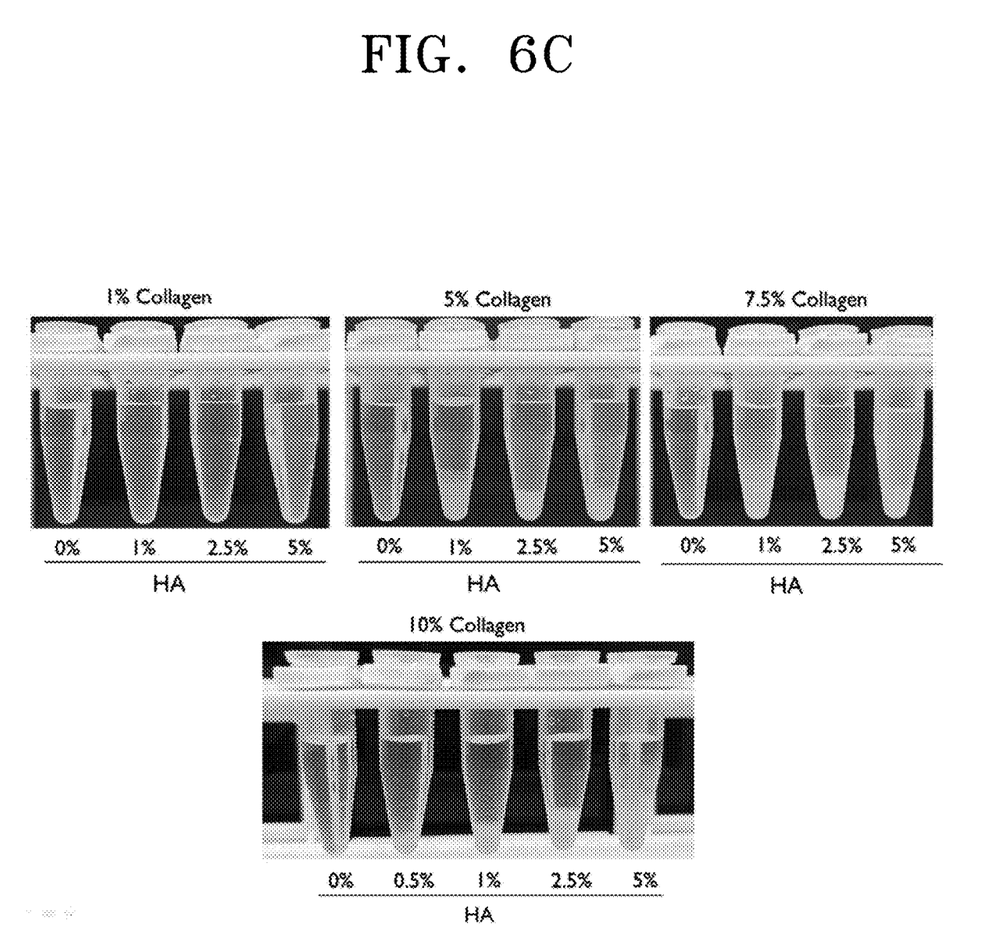
FIG. 6C shows images of microgel suspension that were prepared with collagen at fixed concentration and hyaluronic acid added at varying concentrations and giving agitation to break the resulting hydrogel into microgel which were taken after sedimentation.
Figure 7:
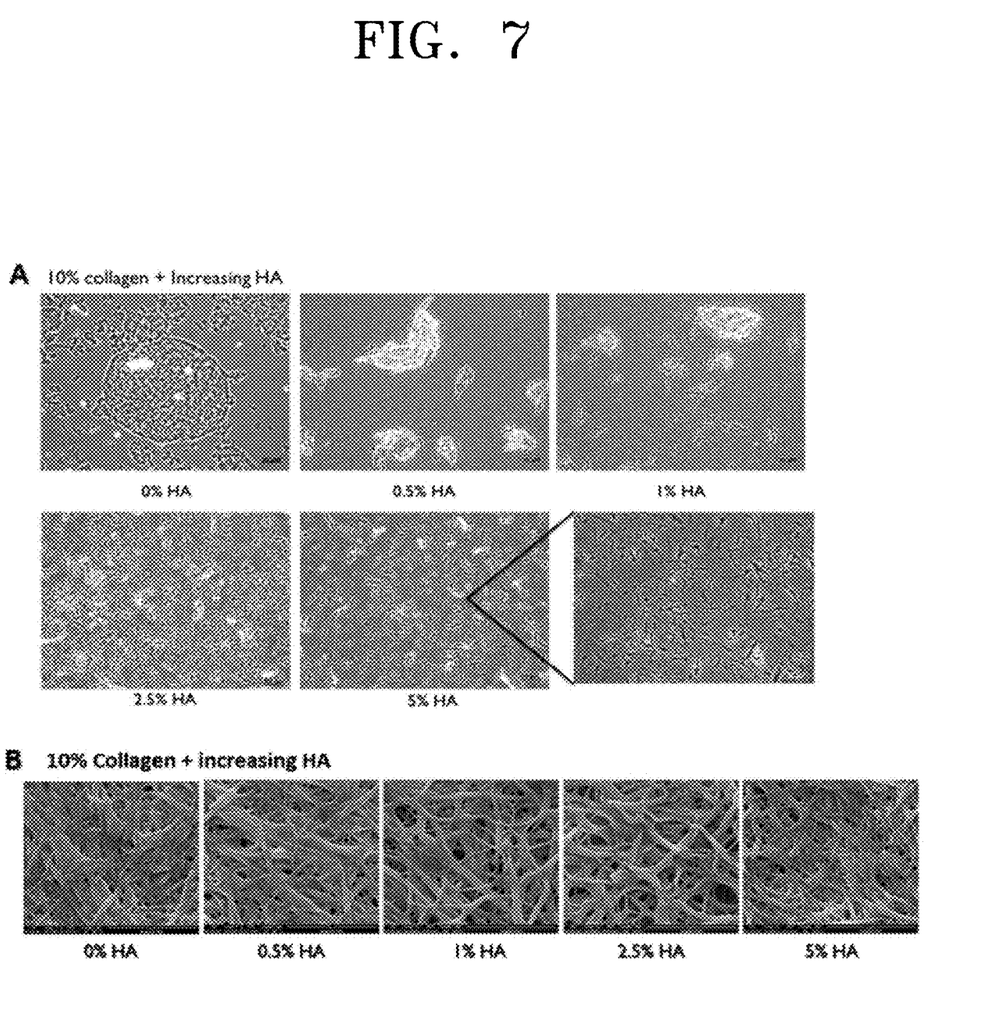
FIG. 7 shows images of collagen-hyaluronic acid microgel suspension that were prepared by giving agitation to collagen-hyaluronic acid comprising 10% (w/v) of collagen and varying concentrations of hyaluronic acid. Prepared microgel particles were observed under a light microscope (FIG. 7A), and the prepared microgel were observed using SEM (FIG. 7B) to show detailed structures.
Figure 8:
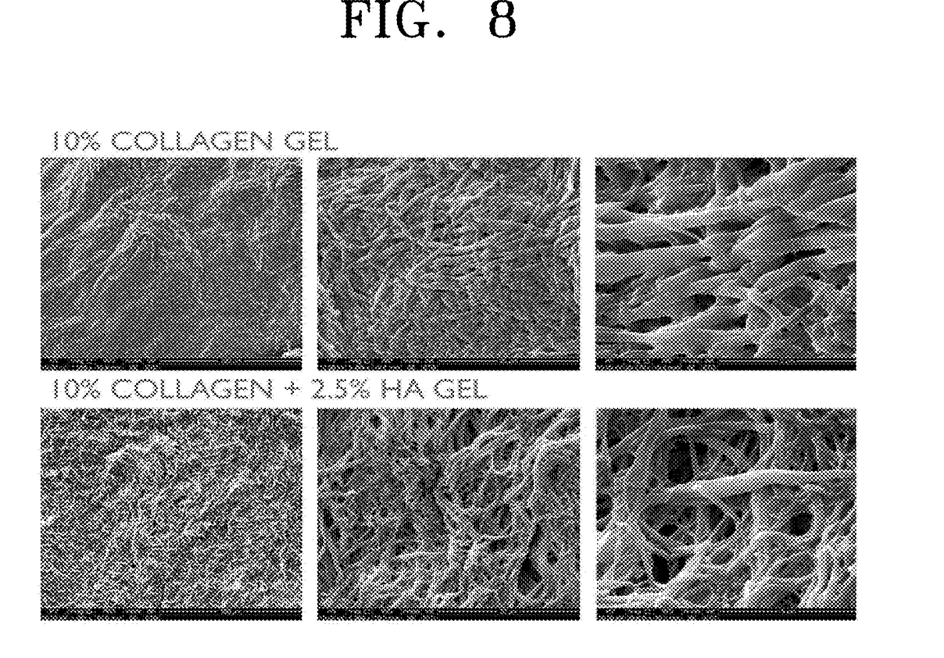
FIG. 8 shows SEM images of hydrogels prepared using 10% (w/v) of collagen alone, and when 2.5% (w/v) of hyaluronic acid is added to 10% (w/v) of collagen.

Experiments were performed to investigate the concentration of hyaluronic acid for forming an optimum microgel through electrostatic interaction between positively charged collagen and negatively charged hyaluronic acid. The collagen was mixed with hyaluronic acid, thereby finally preparing collagen hydrogel comprising 1% (w/v), 5%, 7.5%, and 10% collagen added to 0% (w/v), 0.5%, 1%, 2.5%, and 5% of hyaluronic acid. In order to prepare microgel suspensions, each 10 µL of individually prepared hydrogel was added to 1 mL of distilled water and broken into a microgel suspension by giving agitation using a bead beater at 2000 opm for 10 seconds. Thereafter, the microgel suspension was subjected to sedimentation and then allowed to stand undisturbed at room temperature for 24 hours to prepare a microgel. Images showing hydrogels containing collagens with hyaluronic acid added at varying concentrations are shown in FIG. 6A, images of prepared microgel suspension having collagen-hyaluronic acid of various concentrations are shown in FIG. 6B, images of microgel suspension after sedimentation are shown in FIG. 6C. The morphology of microgel particles of 10% collagen and increasing concentrations of hyaluronic acid, as observed under the light microscope, are shown in FIG. 7A, and SEM images showing detailed structures of hydrogels having 10% collagen with varying concentrations of hyaluronic acid are shown in FIG. 7B. In addition, results confirmed from SEM images of microgels when 10% (w/v) of collagen is used alone, and when 2.5% (w/v) of hyaluronic acid is added to 10% (w/v) of collagen are shown in FIG. 8.

As confirmed from FIGS. 6A to 6C, when 1% collagen was added, a white precipitate was not apparently visible at any concentration of hyaluronic acid added to the collagen, indicating very little or no formation of microgel particles. Then, microgels were apparently visible from addition of 5% to 10% collagen, and microgel suspension resulting after sedimentation were turbid with increasing concentrations of hyaluronic acid. It was confirmed that a large amount of white precipitates was visible at hyaluronic acid concentrations of 2.5% or more. As shown in FIGS. 7A and 7B, it was found that the shapes and sizes of collagen microgels appeared more uniform in size and fibrous in shape increasing concentrations of hyaluronic acid. It was found that when 0.5%, 1% and 2.5% of hyaluronic acid were added, the microgels particles had sizes ranging from 100 μm to 200 μm. In addition, when 5% of hyaluronic acid was added, microgel particles having a size ranging from 20 μm to 40 μm appeared and the microgels had a fibrous shape.

Figure 9:
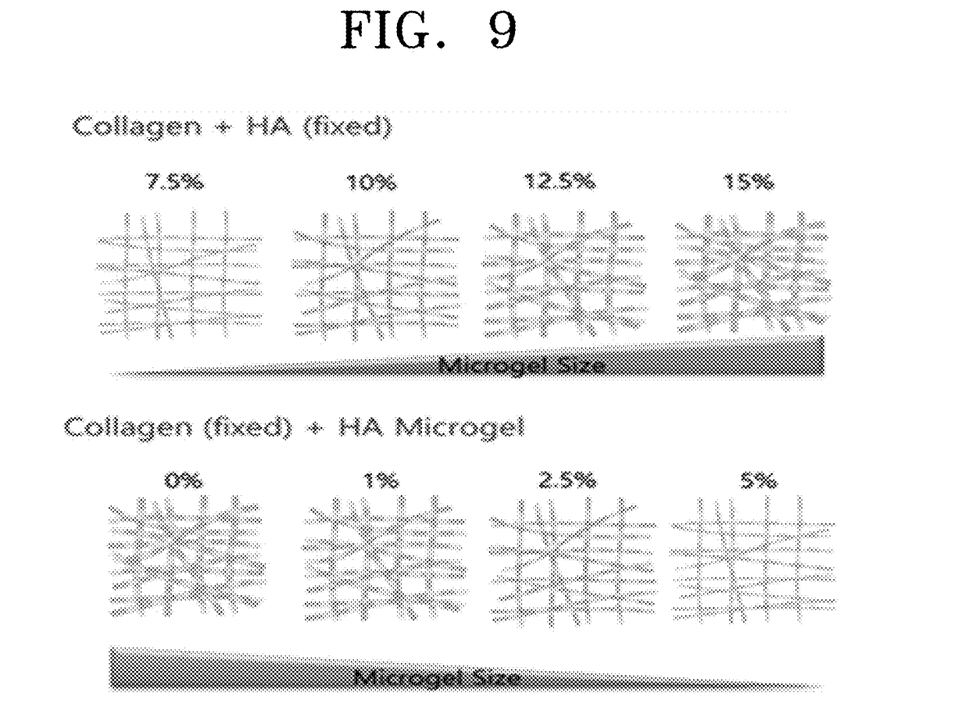
FIG. 9 are schematic drawing showing features (viscoelasticity and microgel size) of microgel fibers produced when concentrations of collagen and hyaluronic acid are varied.

To sum up, as shown in FIG. 9, it was found that at higher concentrations of collagen, the viscoelasticity of collagen became higher and the sizes of microgels produced were correspondingly increased, while, at lower concentrations of collagen, the collagen had a smaller density and collagen fibers became thinner and had lower viscoelasticity. When hyaluronic acid was added to a collagen microgel, collagen fibrillogenesis seemed inhibited due to the hyaluronic acid added, as indicated by thinner collagen fibers, resulting in lowered viscoelasticity, allowing microgels to be effectively made. In addition, microgel particles had smaller sizes with increasing concentrations of hyaluronic acid added, suggesting that production of microgel particles having an optical viscoelasticity and size was achieved by investigating the optimum concentration of collagen and concentrations of hyaluronic acid added thereto.

EXAMPLE 5. IDENTIFICATION OF PH IN SOLUTION FOR FORMING OPTIMUM MICROGEL

Since a microgel was formed through electrostatic interaction between negatively charged hyaluronic acid and positively charged collagen, experiments for confirming which pH level enabled an optimal microgel to be formed were performed. Collagen was mixed with hyaluronic acid, thereby finally preparing a collagen hydrogel comprising 2.5% of hyaluronic acid added to 10% of collagen. In order to prepare microgel suspension, each 10 μL of collagen gel solutions was added to 1 mL of distilled water that was pre-adjusted to pH ranging from 3 to 11 and then broken into a microgel suspension through vortexing. The pH level of distilled water was adjusted using NaOH or HCl. Then, the microgel suspension was subjected to sedimentation and allowed to stand undisturbed at room temperature for 24 hours. Images of microgel suspensions are shown in FIG. 10, and measurement results of zeta potentials of microgel suspension at various pH levels are shown in FIG. 11.

Figure 10:
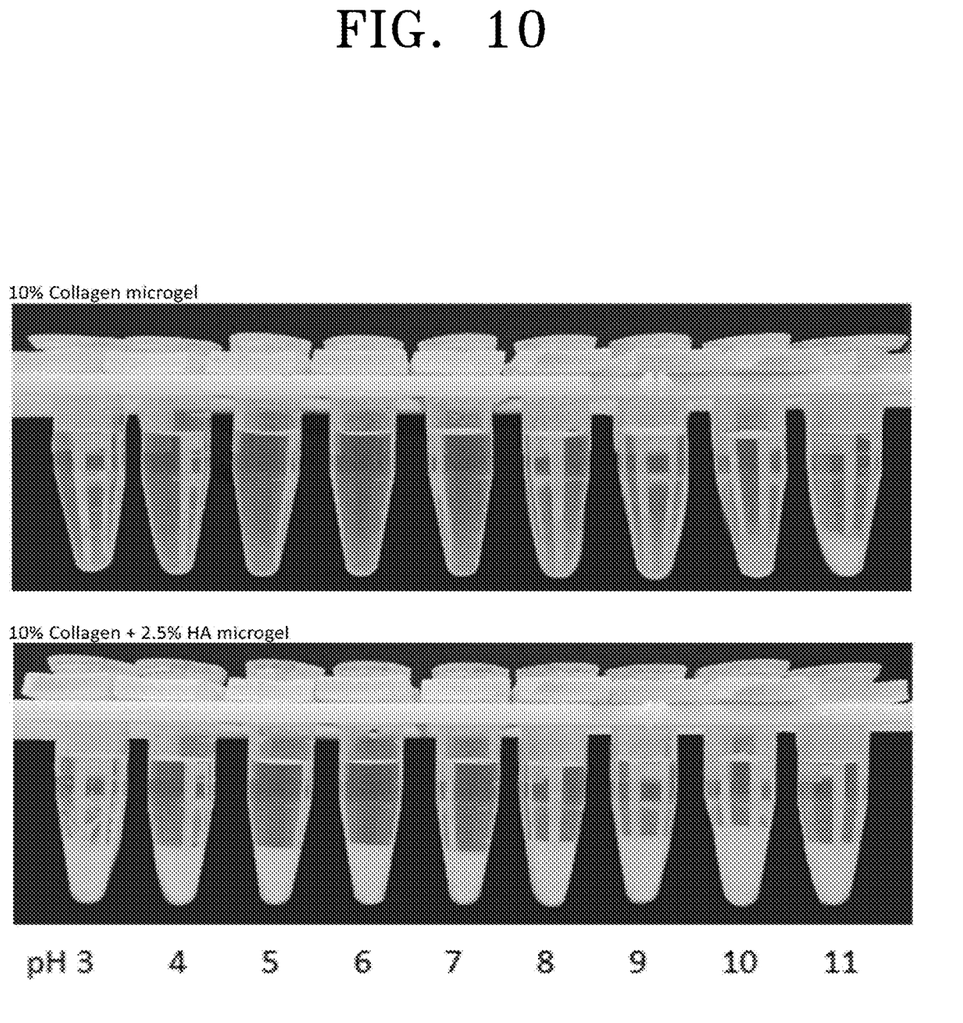
FIG. 10 shows images of collagen-hyaluronic acid microgel suspensions of collagen-hyaluronic acid with varying pH levels.
Figure 11:
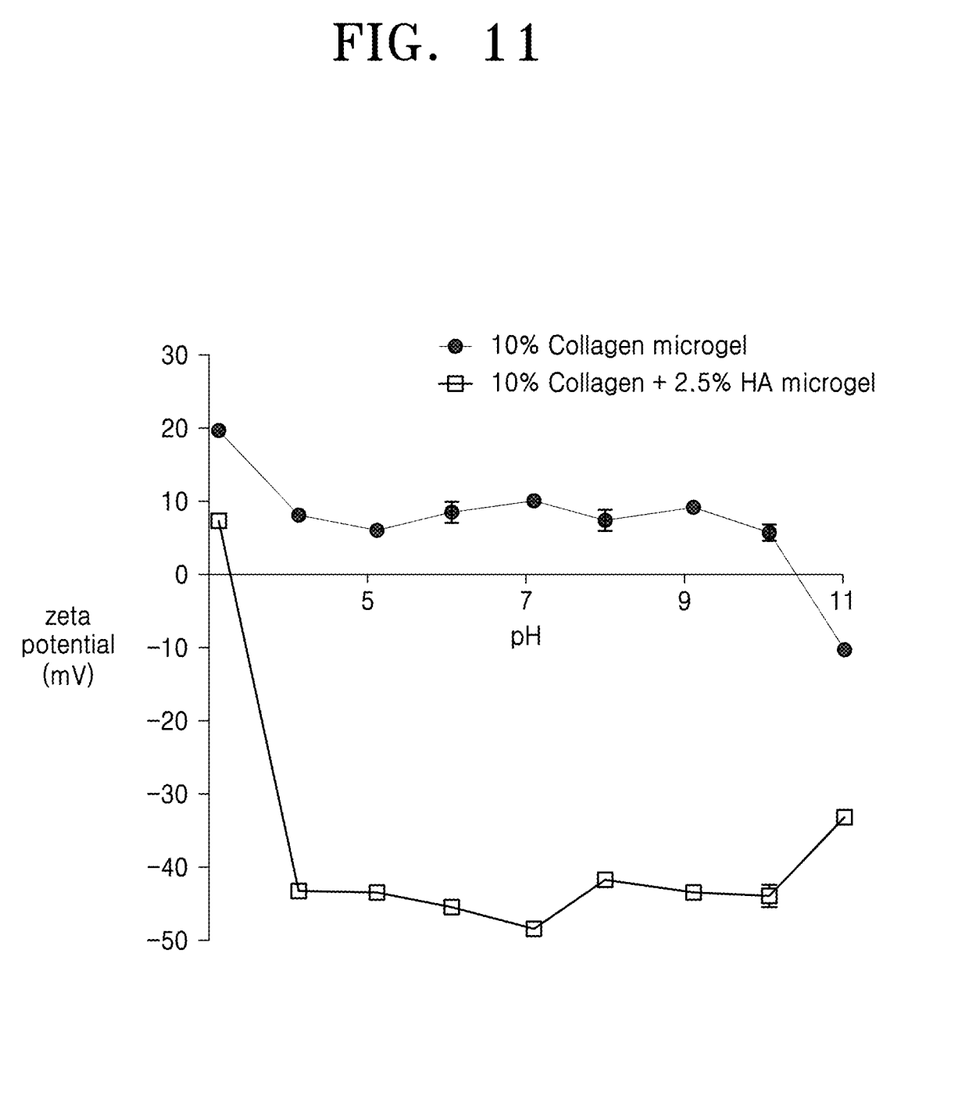
FIG. 11 shows measured zeta potential values of microgel suspension measured at various pH levels.
Figure 12:
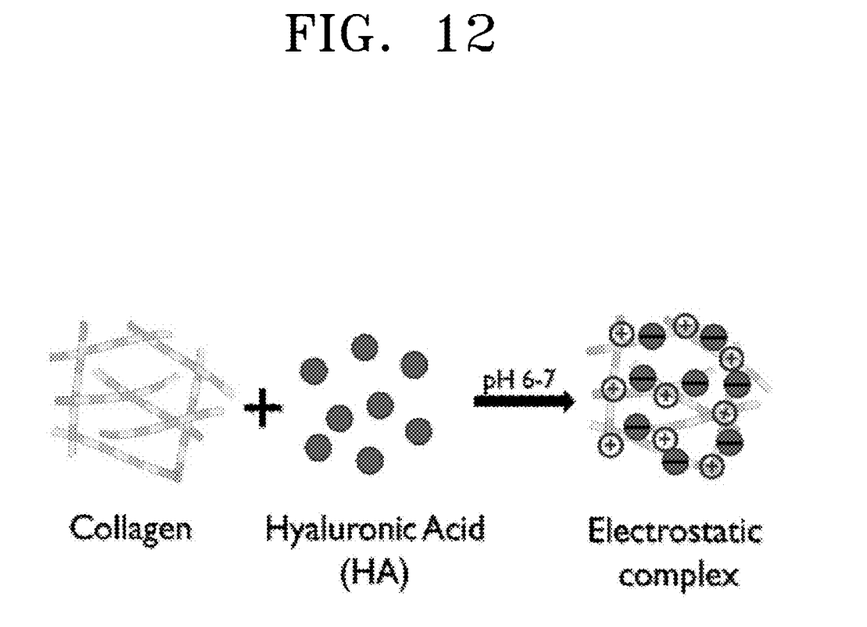
FIG. 12 is a schematic illustration of electrostatic complex forming between collagen and hyaluronic acid at physiological pH of suspension.

As shown in FIG. 10, it was found that white precipitates were not visibly apparent in the microgel comprising 10% collagen only when the pH range was 3 to 10. However, white precipitates were observed in the pH range of 4 to 11 in the microgel suspension having 2.5% of hyaluronic acid added to 10% of collagen, confirming that the microgel was effectively formed in the above pH range, while, at pH 3, turbid precipitates were observed by naked eye. Accordingly, it was confirmed that the pH level for forming the optimum collagen-hyaluronic acid microgel was in the range of 4 to 11. In addition, as confirmed from FIG. 11, the microgel comprising only collagen showed positive zeta potentials for the most part of the pH range. However, the collagen-hyaluronic acid microgel showed relatively constant zeta potential values of about −50 my to about −30 my in the optimum pH range of 4 to 11.

The microgel composition according to an aspect is composed of natural biocompatible substances and is non-toxic and has high mechanical stability or long persistence, and thus can be effectively used to make microgel, a three-dimensional scaffold composition, and a tissue-engineering scaffold.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope of the disclosure as defined by the following claims.

What is claimed is:

1. A microgel composition comprising 10% (w/v) of collagen and 2.5% (w/v) to 5% (w/v) of hyaluronic acid,
   wherein the composition has a zeta potential of −50 mV to −30 mV,
   wherein the composition has a pH of 4 to 11, and
   wherein the microgel is in the form of a nonwoven fabric; a woven fabric; a knitted fabric; a fiber bundle; a cylinder including a fiber bundle and a tube into which the fiber bundle is inserted; or a combination of two or more thereof.

2. The microgel composition of claim 1, wherein the microgel has a size of 10 μm to 250 μm.

3. The microgel composition of claim 1, wherein the composition is a cell-laden microgel.

4. The microgel composition of claim 1, wherein the composition does not comprise a chemical crosslinking agent.

5. A three-dimensional scaffold comprising 10% (w/v) of collagen and 2.5% (w/v) to 5% (w/v) of hyaluronic acid,
   wherein the scaffold has a zeta potential of −50 mV to −30 mV, and
   wherein the scaffold is in the form of a nonwoven fabric; a woven fabric; a knitted fabric; a fiber bundle; a cylinder including a fiber bundle and a tube into which the fiber bundle is inserted; or a combination of two or more thereof.

6. A scaffold for tissue engineering, comprising 10% (w/v) of collagen and 2.5% (w/v) to 5% (w/v) of hyaluronic acid,
   wherein the scaffold has a zeta potential of −50 mV to −30 mV, and
   wherein the scaffold is in the form of a nonwoven fabric; a woven fabric; a knitted fabric; a fiber bundle; a cylinder including a fiber bundle and a tube into which the fiber bundle is inserted; or a combination of two or more thereof.

7. A method of preparing a microgel composition, the method comprising:
   forming an electrostatic collagen-hyaluronic acid complex by reacting 10% (w/v) of collagen and 2.5% (w/v) to 5% (w/v) of hyaluronic acid;
   preparing a dispersion of a microgel by breaking the collagen-hyaluronic acid complex; and adjusting pH level of the dispersion to 4-11,
   subjecting the dispersion of the microgel to natural sedimentation,
   wherein the composition has a zeta potential of −50 mV to −30 mV, and
   wherein the microgel is in the form of a nonwoven fabric; a woven fabric; a knitted fabric; a fiber bundle; a cylinder including a fiber bundle and a tube into which the fiber bundle is inserted; or a combination of two or more thereof.

8. The method of claim 7, wherein the subjecting of the dispersion to natural sedimentation is performed in a temperature range of 20-30° C. for 12-36 hours.

* * * * *